United States Patent [19]

Goudal et al.

[11] Patent Number: 4,582,580

[45] Date of Patent: Apr. 15, 1986

[54] PROCESS FOR THE SEPARATION OF IMMUNOGLOBULINS FROM COLOSTRUM

[75] Inventors: Raymond Goudal; Philippe Huart, both of Vendome; Victor Sanchez, Ramonville-Saint Agne; Jean Mahenc, Portet sur Garonne, all of France

[73] Assignee: Fromageries Bel, Paris, France

[21] Appl. No.: 460,905

[22] Filed: Jan. 25, 1983

[30] Foreign Application Priority Data

Jan. 27, 1982 [FR] France ................................. 82 01230

[51] Int. Cl.$^4$ ............................................. B01D 13/02
[52] U.S. Cl. .................................. 204/182.6; 210/669; 260/120
[58] Field of Search ............... 204/180 P, 301, 180 R, 204/180 B, 182.6; 210/645, 669; 260/120

[56] References Cited

U.S. PATENT DOCUMENTS

| | | | |
|---|---|---|---|
| 3,399,972 | 9/1968 | Skeggs et al. | 204/180 P |
| 3,663,684 | 5/1972 | Freedman et al. | 436/539 |
| 4,009,257 | 2/1977 | Thomas et al. | 424/101 |
| 4,100,149 | 7/1978 | Meiller et al. | 260/112 R |
| 4,276,140 | 6/1981 | Jain | 204/180 P |
| 4,322,275 | 3/1982 | Jain | 204/180 P |
| 4,351,710 | 9/1982 | Jain | 204/180 P |
| 4,437,967 | 3/1984 | Sanchez et al. | 204/180 P |

OTHER PUBLICATIONS

Chemical Abstracts, vol. 79, No. 17, Oct. 29, 1973, p. 286, #103430a, by M. Janusz et al., "Immunoglobulins of Colostrum. I. Preparation and Identification of Oxine Colostral Immunoglobulins."

Chemical Abstracts, vol. 79, No. 17, Oct. 29, 1973, p. 286, #103431b, by M. Janusz et al., "Immunoglobulins of Colostrum. II. Preparation and Identification of Bovin Colostral Immunoglobulins."

Chemical Abstracts, vol. 85, No. 9, Aug. 30, 1976, p. 426, #61211w, by S. S. Stone et al., "Chromatographic Separation of Gram Quantities of Immunoglobulins from Porcine Colostrum Against Transmissible Gastroenteritis Virus."

Chemical Abstracts, vol. 77, No. 17, Oct. 23, 1972, p. 285, #112325f, by C. Sarmanioti et al., "Chromatographic Fractionation of Horse Serum and Colostral Globulins and Separation of Immunoglobulins G & G(T)".

Primary Examiner—John F. Niebling
Assistant Examiner—B. J. Boggs, Jr.
Attorney, Agent, or Firm—Young & Thompson

[57] ABSTRACT

The present invention relates to a process for the separation of the immunoglobulins present in colostrum, wherein a milk of colostrum or a serum of colostrum is fractionated by liquid electrophoresis, the immunoglobulin-enriched fraction is recovered and said immunoglobulin-enriched fraction is then fractionated by ion-exchange chromatography.

5 Claims, No Drawings

PROCESS FOR THE SEPARATION OF IMMUNOGLOBULINS FROM COLOSTRUM

DESCRIPTION

The present invention relates to a process for the separation of immunoglobulins from colostrum.

Colustrum is the mammary secretion of female mammals, secreted during the days that follow parturition. Its composition and appearance are very different from those of milk and remain so until the seventh day. Its characteristics are, among others, richness in proteins, especially in immunoglobulins of which the content varies from 6 to 10% on first milking to 0.09% which is the normal content of milk. These proteins, and especially the immunoglobulins, are of great interest, especially in the medical and pharmaceutical field. They can, in particular, be added to foods of new-born calves and serve to increase their disease immunity, or may be used in medicine, pharmaceuticals or human foodstuffs and particularly for children's foods. It has been calculated that the quantity of immunoglobins contained in colostrum produced during the first seven consecutive milkings is equivalent to that contained in the blood rejected by slaughterhouses. There is therefore important to find a process for the separation of the immunoglobulins present in colostrum.

A process for separating proteins by means of ion-exchange chromatography is disclosed in U.S. Pat. No. 4,100,149. Ion-exchange materials are used, for this purpose, consisting of porous particles on the surface of which are grafted ion-exchange groups. This patent describes the separation of immunoglobulins from human serum from which lipids have been removed on an anionic exchanger material (consisting of particles of silica coated with a polymer having anionic sites), the immunoglobulins being recovered in the effluent "in an electrophoretically pure state" while the other proteins are fixed.

Yet, when one attempts to operate in the same way with a colostrum serum, one only obtains in the effluent an immunoglobulin-enriched fraction which still contains an important proportion of other proteins.

The Applicant has found that it was possible to separate the immunoglobulins present in colostrum if the colustrum milk or colustrum serum is fractioned by electrophoresis before carrying out the ion-exchange chromatography.

Thus this invention relates to a process for the separation of the immunoglobulins present in colostrum wherein a milk of colostrum or a serum of colostrum is fractioned by liquid electrophoresis, the immunoglobulin-enriched fraction is recovered and the said immunoglobulin-enriched fraction is then fractioned by ion-exchange chromatography.

The raw material used is, preferably, colostrum from cows but may be from any other mammal.

Fractionation is not performed on natural colostrum but on milk of colostrum from which the cream has been removed or, preferably, on serum of colostrum which has been subject to skimming and coagulation in order to remove the casein. Said coagulation may be carried out by adding rennet of strength 1/10,000 on the basis of about 0.1 ml/l, or by acidic precipitation.

The first fractionation used in the present invention is fractionation by liquid electrophoresis.

This type of fractionation generally consists of fractionating a solution comprising at least two groups of substances dissolved in a liquid in order to obtain at least two liquid fractions one of which contains the first group of substances with a relative richness higher than that of the original solution and the other contains the second group with a relative richness higher than that of the said solution; for this purpose, the initial solution is transferred into at least one fractionation chamber limited by two semi-permeable membranes on two principal opposing sides and an electric field is applied to the said chamber so as to cause migration of the groups of substances in relation to their electrical and physical characteristics, causing natural convection by the effect of concentration gradients with the creation of ascending and descending flows of liquid, and the liquid is withdrawn from at least two different zones in order to collect said fractions.

Fractionation may, in particular, be performed in accordance with the process described in patent No. FR 2 493 725 and the Doctor of Engineering Thesis of the Faculty of Science of Toulouse: preparation of proteinaceous fractions of serum or of blood plasma by electrophoresis, P. Espenan, 1980. An electric field is used in this process to provide through at least one of the semi-permeable membranes, a high-speed ion-exchange between the original solution contained in the fractionation chamber or chambers and an auxiliary solution placed on the other side of the said membrane and containing ions of the type suitable to pass through the said membrane and to increase the differences of migration speed of the substances from the original solution.

In accordance with the preferred method of use of the process, the original solution is admitted into a series of fractionation chambers that are side-by-side and separated from each other by the semi-permeable membranes, while the auxiliary solution is placed either side of the two end chambers in two storage compartments each of which is separated by a semi-permeable membrane from the neighboring fractionation chamber and ion-exchange is performed at high speed under the effect of the electrical field, from the said storage compartments through the fractionation chambers, from one to the next.

This process thus provides a means of providing, in one operation and in the same device, an adaptation of the original solution to give it the appropriate properties needed to accentuate the differences of migration of the substances, firstly, and the specific operation of fractionating the said substances, secondly. The electric field used for fractionation also serve to generate rapid ion-exchange through the membranes between the original solution contained in the fractionation chambers and the auxiliary solution contained in the storage compartments. Operations of preliminary preparation are thus radically eliminated, especially the dialysis that is required in traditional processes and also the corresponding disadvantages; moreover, the original solution no longer has to be diluted and the process can be applied to natural solutions in the state in which they are produced or collected.

This process has already been used for fractionation and recovery of plasma immunoglobulins in order to separate an albumin-rich fraction and a fraction rich in γ-globulins.

The separation by liquid electrophoresis in the present invention is performed advantageously at a pH of 6 to 7, preferably 6.3–6.4 (that is, in practice generally with no modification of pH) and at a temperature of 4°

C. to 25° C., preferably 4° C. A fraction that is relatively richer at the nature state, in immunoglobulins than the original concentration is recovered at the top of the electrophoresis device and a fraction relatively richer in albumins at the bottom. To give an example, taking a solution of the following composition (in percent by weight):

| | |
|---|---|
| immunoglobulin content | 77% |
| α-lactalbumin content | 4.5% |
| β-lactoglobulin content | 14.4% |
| serum albumin content | 3.0% |

The following composition (in percent weight), respectively, in the fractions relatively richer in immunoglobulins and in albumins is obtained.

| | Immunoglobulin-rich fraction (top of device) | Albumin-rich fraction (bottom of device) |
|---|---|---|
| Immunoglobulins | 83 | 67 |
| α-lactalbumin | 1.2 | 6.4 |
| β-lactoglobulin | 8.0 | 20.0 |
| Serum albumins | — | 5.6 |

The quantity of immunoglobulins recovered at the top of the device depends on operating conditions and, among others, on the rate of withdrawal; it can reach 70 to 80%.

The second fractionation process used in the present invention is fractionation by ion-exchange chromatography. It consists of submitting the fraction rich in immunoglobulins obtained by the first fractionation process, to ion-exchange chromatography.

The immunoglobulin-rich fraction is precolated, for this purpose, through a column filled with ion-exchange particles.

As ion-exchange particles, use may be made advantageously of the porous articles sold under the name of "Sphérosil" by the RHONE-POULENC COMPANY and described in the above U.S. patent, which belong to the following types:
Sphérosil, Q MA, strong basic ion-exchanger,
Sphérosil, C, very weak acidic ion-exchanger,
Sphérosil, S, strong acidic ion-exchanger,
Sphérosil, X OB 0 15, very weak acidic ion-exchanger.

Sphérosils Q MA, C and S are obtained by fixing ion-exchanger resins on beads of porous silica (X OB 0 15).

Any other type of ion-exchanger that provides selective fixing of proteins may be used, for example, grafted celluloses such as the anion-exchanger resins "Trisacryl" sold by I.B.F.

Anionic exchangers are used preferably, such as Sphérosil Q MA exchangers that provide a means of directly treating the immunoglobulin-rich fraction obtained during the first stage, without modifying the pH(between 6 and 7) and obtaining a high yield of immunoglobulins in the effluent that leaves the column. This affords the advantage of preventing any risk of denaturation of the immunoglobulins by fixation on the ion-exchangers.

A solution of proteins can thus be obtained containing 98 to 100% of immunoglobulins.

The chromatography can be performed at a temperature from 4° to 25° C. and, advantageously, at 4° C.

The solution of immunoglobulins can then be post-treated, by drying, concentration, dialysis or ultrafiltration for the purpose of later use, for example.

The present invention is illustrated by the following examples:

EXAMPLE 1

A-Fractionation by liquid electrophoresis

A colostrum serum of pH of 6.3 and the following composition (in g/l), is used as starting material

| | |
|---|---|
| Immunoglobulins | 65.5% |
| α-lactalbumin | 8.7% |
| β-lactoglobulin | 15.2% |
| Serum-albumins | 6.3% |

This colostrum serum is fractionated by electrophoresis using the device described in application No. FR 2 493 725 at a temperature of 4° C.

This device comprises five fractionation chambers separated by semi-permeable cellophane membranes of which the active surface of each is 60 cm$^2$. Each chamber is 3 mm thick and comprises a frame that divides it into eleven vertical channels against which the membranes bear.

The auxiliary solution circulating in the side storage compartments is a mixture of $Na_2HPO_4$; and $KH_2PO_4$; at a saline concentration of 0.05M and at a pH of 6.25. A solution of $Na_2HPO_4$ and $KH_2PO_4$ also circulates in the ajoining electrode compartments but at a concentration of 0.2M.

Three tests have been performed of which the operating conditions are given in Table I.

TABLE I

| | Withdrawal flow rate at top output | Withdrawal flowrate at bottom output | Difference of potential between the 2 end membranes of the withdrawal chambers | Amperage |
|---|---|---|---|---|
| Test I | 105 | 105 | 6 V | 0.8 A |
| Test II | 70 | 70 | 6 V | 0.8 A |
| Test III | 105 | 35 | 6 V | 0.77 A |

Two liters of colostrum serum were treated by electrophoresis for each test.

The quantity of each protein recovered at the top and the bottom of the device is given in Table II with the volume of solution recovered.

| | Test I | | Test II | | Test III | |
|---|---|---|---|---|---|---|
| | Top | Bottom | Top | Bottom | Top | Bottom |
| Immunoglobulins | 68 | 63 | 75 | 52 | 102 | 27 |
| α-lactalbumins | 6 | 11,4 | 4,8 | 12,2 | 7 | 10 |
| β-lactoglobulins | 6 | 24,4 | 5,3 | 25,0 | 7 | 22,2 |
| Serum albumins | 0,6 | 11,9 | 0,5 | 11,8 | 1 | 11,2 |
| Volume collected (in liters) | 1 | 1 | 1 | 1 | 1,5 | 0,5 |

It can be seen that the fraction collected at the device top is more concentrated in immunoglobulins than the original fraction.

The quantity of immunoglobulins obtained at the device top depends on experimental conditions and approaches 80% in the third test.

An analysis of radial immunodiffusion (the Mancini method) shows that denaturation is very low. It is seen that, by immunoelectrophoresis, all the immunoglobulins present in the colostrum processed ($IgG_1$, IgA and IgM) are collected.

B-Fractionation by ion-exchange chromatography 200 ml of the liquid obtained in Test I at the device top and enriched in immunoglobulins are percolated through a column of anion exchanger Q MA Sphérosil, containing 64 g of Sphérosil Q MA at pH 6.3 and with the Sphérosil at a temperature of 4° C. Flowrate is 300 ml/h.

The results are given in Table III.

TABLE III

|  | Grammes of proteins supplied to column | Effluent, grammes of proteins | Grammes of proteins fixed on column |
|---|---|---|---|
| Immunoglobulins | 13.6 | 8 to 10 | 3.6 to 5.6 |
| α-lactalbumin | 1.2 | 0 | 1.2 |
| β-lactoglobulin | 1.2 | 0 | 1.2 |
| Serum albumins | 0.12 | 0 | 0.12 |

The effluent only contains immunoglobulins. The electroimmunodiffusion analysis moreover indicates that they are exclusively $IgG_1$ and, more specifically, the fraction of the $IgG_1$'s with the highest isoelectric point. This fraction should also contain the lactotransferrins of which the isoelectric point is 7.8

The albumins are recovered by elution with 0.1N HCl, as are the other immunoglobulins, $IgG_1$, IgA abd IgM.

Similar results are obtained with the liquid that leaves the top of the electrophoresis cell in Tests II and III.

The average fixation capacity of the Q MA Sphérosil is, in the present case, 110 mg/g.

COMPARATIVE EXAMPLE

We start with a sample of 250 ml of colostrum serum from the first milking, with a total protein content of 104 g/l and with the following composition of immunoglobulins and of serum albumins.

|  | % | Grammes of proteins treated |
|---|---|---|
| Immunoglobulins | 77.7 | 19.4 |
| α-lactalbumin | 2.4 | 0.6 |
| β-lactoglobulin | 15.4 | 3.8 |

-continued

|  | % | Grammes of proteins treated |
|---|---|---|
| Serum albumins | 3.0 | 0.8 |

This colostrum serum is percolated directly through a column of Sphérosil Q MA ion-exchanger containing 64 g of resin (identical to that used in example 1). The fixation capacity is 96 mg/g at pH 6.3 and at 4° C. with flowrate 300 ml/h.

The compositions of the effluent and of the eluate obtained with a 0.1N solution of HCl are as follows:

|  | % | Effluent Grammes recovered | % | Eluate Grammes recovered |
|---|---|---|---|---|
| Immunoglobulins | 89.6 | 15.4 | 45.4 | 2.5 |
| α-lactalbumin | 1.5 | 1.6 | 54.6 | 3.0 |
| α-lactoglobulin | 8.2 | | | |
| Serum albumins | 0.7 | | | |

It is seen that the effluent is enriched in immunoglobulins but still contains a considerable fraction of other proteins.

Having now described our invention what we claim as new and desire to secure by Letters Patent is:

1. A process for the separation of the immunoglobulins present in colostrum, wherein a colostrum milk or a colostrum serum is directly fractionated by liquid electrophoresis at a pH of 6 to 7, the immunoglobulin-enriched fraction is recovered, the said fraction is directly, with the same said pH, percolated through a column of anion-exchanger particles, and the immunoglobulins are recovered from the effluent that leaves the column.

2. A process as claimed in claim 1, wherein the substance treated is a colostrum serum.

3. A process as claimed in claim 1, wherein said liquid electrophoresis fractionation is performed at a temperature of 4° to 25° C.

4. A process as claimed in claim 1, wherein ion-exchange chromatography fractionation is performed at a temperature of 4° to 25° C.

5. A process as claimed in claim 1, wherein said pH is 6.3–6.4.

* * * * *